(12) United States Patent
Kim et al.

(10) Patent No.: US 10,078,064 B2
(45) Date of Patent: Sep. 18, 2018

(54) APPARATUS FOR MEASURING POLLUTION LEVEL OF SURFACE OF PHOTOVOLTAIC MODULE

(71) Applicant: MAIN-ENERGIA INC., Daejeon-si (KR)

(72) Inventors: Taik Nam Kim, Yongin-si (KR); Suk Ho Sinn, Chungju-si (KR)

(73) Assignee: MAIN-ENERGIA INC., Daejeon-si (KR)

( * ) Notice: Subject to any disclaimer, the term of this patent is extended or adjusted under 35 U.S.C. 154(b) by 225 days.

(21) Appl. No.: 15/233,413

(22) Filed: Aug. 10, 2016

(65) Prior Publication Data
US 2018/0045661 A1    Feb. 15, 2018

(51) Int. Cl.
| | |
|---|---|
| *G01N 27/00* | (2006.01) |
| *G01N 27/04* | (2006.01) |
| *G01N 33/552* | (2006.01) |
| *G01N 33/553* | (2006.01) |
| *H02S 50/00* | (2014.01) |

(52) U.S. Cl.
CPC ........... *G01N 27/04* (2013.01); *G01N 33/552* (2013.01); *G01N 33/553* (2013.01); *H02S 50/00* (2013.01)

(58) Field of Classification Search
CPC ...... G01N 27/04; G01N 27/00; G01N 33/552; G01N 33/553; H02S 50/00
USPC .................................. 422/68.1, 82.01, 82.02
See application file for complete search history.

(56) References Cited

U.S. PATENT DOCUMENTS

| | | | | |
|---|---|---|---|---|
| 4,836,012 A | * | 6/1989 | Doty .................. | G01N 33/0027 136/255 |
| 6,455,320 B1 | * | 9/2002 | Danz ..................... | G01N 21/31 422/82.08 |
| 2009/0056789 A1 | * | 3/2009 | Draganov ............... | H01L 31/18 136/246 |
| 2011/0308318 A1 | * | 12/2011 | Magnussen ........... | G01J 1/0492 73/649 |

* cited by examiner

*Primary Examiner* — Brian J. Sines
(74) *Attorney, Agent, or Firm* — Im IP Law; C. Andrew Im

(57) ABSTRACT

An apparatus to measure the pollution level of the surface of a photovoltaic module. A resistance change on the surface of a photovoltaic module is sensed to effectively measure the pollution level on the surface of the photovoltaic module and secure a proper cleaning cycle of the module during solar light power generation. The apparatus includes a glass substrate attachably mounted on the surface of a photovoltaic module. A reactive coating layer is coated on one side of the glass substrate, has a structure that pollutants are accumulated on one side surface, and causes a resistance change by contact with the pollutants. A signal processor connected to the reactive coating layer to receive a signal of the resistance change, operationally process the signal to measure a change in the resistance value caused by accumulation of the pollutants, and output a discrimination signal on pollution.

5 Claims, 5 Drawing Sheets

APPARATUS FOR MEASURING POLLUTION LEVEL OF SURFACE OF PHOTOVOLTAIC MODULE

BACKGROUND OF THE INVENTION

Field of the Invention

The present invention relates to an apparatus for measuring the pollution level of the surface of a photovoltaic module, and more particularly, to an apparatus for measuring the pollution level of the surface of a photovoltaic module, which can sense a resistance change on the surface of a photovoltaic module in order to effectively measure the pollution level on the surface of the photovoltaic module and secure a proper cleaning cycle of the module during solar light power generation.

Background Art

Recently, with the resource shortage problem due to exhaustion of energy resources, such as oil or coal, there is a rising interest on new and renewable energy which can replace the existing energies, and so, solar light power generation technology for producing electric energy from solar energy which has been known as a boundless energy source is under the spotlight.

In general, for the solar light generation technology, solar cells equipped in various facilities, such as photovoltaic power plants, factories or houses, which require electric energy, to generate electric power using semiconductor devices providing photovoltaic effect by converting solar energy into electric energy have been widely used.

Here, a plurality of solar cells each of which can generate about 1.5 watt electric power as the smallest unit to generate electricity are connected in series or in parallel so as to be used in the form of a photovoltaic module to output electricity available in the actual life.

However, because the photovoltaic module is covered with tempered glass and dust is always accumulated on the surface of the photovoltaic module due to generation of static electricity and dust scattering, the surface of the photovoltaic module for collecting the rays of the sun is polluted and a power generation rate of the photovoltaic module is reduced by about 10% to 15%, namely, generation efficiency is reduced.

In order to solve the above problem, Korean Patent No. 1126339 (granted on Mar. 6, 2012) discloses a pollution preventing structure for a solar cell which includes: a support plate mounted on an upper end of a pole; an optical sensor mounted on the support plate to measure external illuminance; a plurality of generation panels which are arrayed along an edge of the support plate, and each of which has a solar cell plate mounted on the front side, a light-transmitting material formed on the rear side and an end portion mounted at the edge of the support plate in such a way as to be folded or unfolded by a rotary shaft, a motor connected onto the rotary shaft of the generation panels in order to fold or unfold the generation panels; a rechargeable battery for storing a power source outputted from the solar cell of the generation panel; light emitting means for emitting light by the power source supplied through the rechargeable battery; and a control unit for controlling the motor and charge and discharge of the rechargeable battery according to intensity of illumination measured by the optical sensor, wherein side end portions of the generation panels come into contact with each other when the general panels are folded so as to prevent penetration of moisture or dust which pollute the surface of the solar cell, thereby preventing deterioration in generation efficiency of the solar cells.

However, because the photovoltaic module has a structure to be opened and closed overall, the pollution preventing structure for the solar cell according to the above-mentioned prior art is complicated in structure, it costs a lot to manufacture and install products, is difficult to apply to places requiring mass production of electricity, such as photovoltaic plants, and is inapplicable to the previously installed photovoltaic modules. Therefore, the pollution preventing structure for the solar cell according to the above-mentioned prior art is ineffective.

Moreover, because the pollution preventing structure for the solar cell according to the above-mentioned prior art has the structure to be folded or unfolded according to external illuminance, it can temporarily prevent pollution of the photovoltaic module just in the folded state of the apparatus. So, because the photovoltaic module is still exposed to pollution factors, such as dust, during the photovoltaic generation process, it cannot prevent pollution of the surface of the photovoltaic module, and generation efficiency of the photovoltaic module is deteriorated as time passes.

Therefore, in order to maintain generation efficiency of the photovoltaic module, work to periodically clean and wash the surface of the photovoltaic module is essential, and in order to make a manager recognize the periodic cleaning work, a measuring device which can sense the pollution level on the surface of the photovoltaic module has been urgently demanded.

CITED REFERENCES

Patent Documents

Patent Reference 1: Korean Patent No. 1126339 (Mar. 6, 2012)

SUMMARY OF THE INVENTION

Accordingly, the present invention has been made in view of the above-mentioned problems occurring in the prior art, and it is an object of the present invention to provide an apparatus for measuring the pollution level of the surface of a photovoltaic module, which can sense an electrical resistance change on the surface of a photovoltaic module to measure the pollution level by pollution factors, thereby being flexibly applied to photovoltaic modules due to its simple structure, lengthening the lifespan of equipment by recognizing the optimum cleaning cycle and increasing photovoltaic effect.

To accomplish the above object, according to the present invention, there is provided an apparatus for measuring the pollution level of the surface of a photovoltaic module including: a glass substrate attachably mounted on the surface of a photovoltaic module; a reactive coating layer which is coated on one side of the glass substrate, has a structure that pollutants are accumulated on one side surface, and causes a resistance change by contact with the pollutants; and a signal processor which is connected with the reactive coating layer to receive a signal of the resistance change, operationally processes the signal of the reactive coating layer to measure a change amount of a resistance value from the resistance change by accumulation of the pollutants, and outputs a discrimination signal on pollution.

The reactive coating layer includes a metal oxide layer which is formed from oxide to cause the resistance change by physical and chemical reactions from accumulation of the pollutants.

The apparatus for measuring the pollution level of the surface of the photovoltaic module according to the present invention further includes: electrode layers which are formed between the upper side of the glass substrate and the reactive coating layer and are made from silver (Ag); and first connection lines which are formed to electrically connect the electrode layers to the signal processor.

The metal oxide layer has a thickness of 1 to 10 μm.

Moreover, the reactive coating layer includes a metal conductive layer formed from electroconductive metal to cause the resistance change by a contact reaction of non-conductive particles from the accumulated pollutants.

The metal conductive layer includes: a first metal thin film layer coated on the upper side of the glass substrate; a graphite conductive layer disposed on the first metal thin film layer; a second metal thin film layer disposed on the graphite conductive layer; and a hole which is formed to penetrate the metal conductive layer from the second metal thin film layer to the graphite conductive layer to induce pollutants to be accumulated.

The first metal thin film layer and the second metal thin film layer have a thickness of about 0.5 to 2 μm and are made of aluminum metal.

The apparatus for measuring the pollution level further includes second connection lines which are respectively derived from the first metal thin film layer and the second metal thin film layer and are electrically connected to the signal processor.

The signal processor includes: an operator part which operationally processes the resistance value from the signal of the reactive coating layer to measure the resistance value; a display part which outputs the resistance value measured in the operator part; a signal judging part which judges whether or not there is any change in the resistance value measured in the operator part; a comparative discrimination part which compares the resistance value measured in the operator part with a reference resistance value set previously to discriminate pollution; and an LED on-off part which turns light on and off to display the result according to the discrimination signal of the comparative discrimination part.

The apparatus for measuring the pollution level further includes a remote control communication part which is communicably connected with a central server of a photovoltaic plant so as to sends the discrimination signal measured in the signal processor to the central server through a computer communication network and to receive a control signal of the central server through the computer communication network so that the signal processor can measure the pollution level.

Because the apparatus for measuring the pollution level of the surface of the photovoltaic module according to the present invention discriminates pollution through a change amount of the resistance value after sensing the electric resistance change by contact with pollutants, the pollution level measuring apparatus lets a manager know the optimum cleaning cycle to recognize necessity of cleaning work and maintain the photovoltaic module clean through the periodic cleaning work, thereby maintaining performance of equipment, lengthening the lifespan of equipment and increasing added value through energy generation by enhancing generation efficiency of the photovoltaic module.

Moreover, the apparatus for measuring the pollution level of the surface of the photovoltaic module according to the present invention can enhance price competitiveness by lowering manufacturing costs and installation costs of equipment because having the simple structure including the glass substrate attachable to the surface of the photovoltaic module, the reactive coating layer and the signal processor, and also enhance effectiveness of products because being flexibly applicable to previously designed photovoltaic modules.

Furthermore, due to the remote control communication part which is communicably connected with a central server of the photovoltaic plant, the apparatus for measuring the pollution level of the surface of the photovoltaic module according to the present invention can measure the pollution level of the photovoltaic modules of the array type in a lump so as to easily maintain and rapidly process the measured result.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
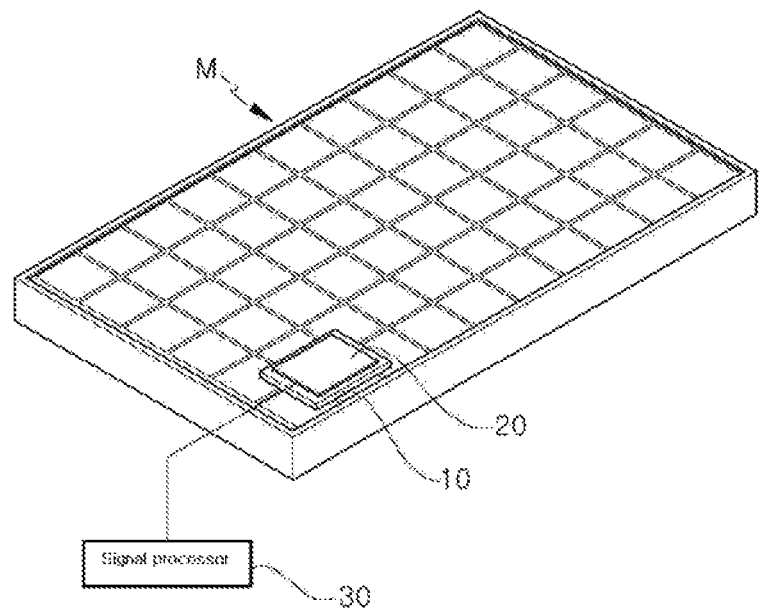
FIG. 1 is a schematic diagram of an apparatus for measuring the pollution level of the surface of a photovoltaic module according to a preferred embodiment of the present invention.

The present invention relates to an apparatus for measuring the pollution level of the surface of a photovoltaic module, which includes: a glass substrate attachably mounted on the surface of a photovoltaic module; a reactive coating layer which is coated on one side of the glass substrate, has a structure that pollutants are accumulated on one side surface and causes a resistance change by contact with the pollutants; and a signal processor which is connected with the reactive coating layer to receive a signal of the resistance change, operationally processes the signal of the reactive coating layer to measure a change amount of a resistance value from the resistance change by accumulation of the pollutants, and outputs a discrimination signal on pollution.

Hereinafter, referring to the drawings, the apparatus for measuring the pollution level of the surface of the photovoltaic module according to preferred embodiments of the present invention will be described in detail.

However, the embodiments of the present invention may be variously modified, and it is not interpreted that the scope of the invention is limited by embodiments described later. The embodiments of the present invention have been given only for those skilled in the art to better understand the present invention, and the shapes, etc. of elements shown in the drawings are exemplarily given to more clearly describe the present invention.

First, as shown in FIG. 1, the apparatus for measuring the pollution level of the surface of the photovoltaic module according to a preferred embodiment of the present invention includes: glass substrate 10, a reactive coating layer 20 and a signal processor 30.

The glass substrate 10 is in the form of a plate having a predetermined thickness and its upper and lower sides are all flat planes.

The glass substrate 10 is located to maintain a state where one side gets in surface contact with the surface of the photovoltaic module (M) which is an object to be measured for measurement of the pollution level.

The glass substrate 10 may be formed to be attachable to the surface of the photovoltaic module (M). That is, the glass substrate 10 may be located on the photovoltaic module (M) to maintain the simple contact state or may be attached to the surface of the photovoltaic module (M) with a predetermined adhesive force.

The reactive coating layer 20 has the structure that pollutants are accumulated on the surface of one side and is coated on one side of the glass substrate 10.

In this specification, pollutants mean particles of about 2.5 to 10 μm having different kinds of dust in the air. For instance, pollutants are materials on the surface of the earth, such as $SiO_2$, $Al_2O_3$, FeO, $Fe_2O_3$, CaO, $K_2O$ and $TiO_2$, secondary ion clusters consisting of gas precursors, such as $NH_4NO_3$ and $(NH_3)_2SO_4$, carbon particles by combustion, and so on.

The reactive coating layer 20 functions to cause a resistance change by contact with the pollutants accumulated on the surface of one side.

The reactive coating layer 20 may be formed from any one of oxide and conductive metal.

Figure 2:
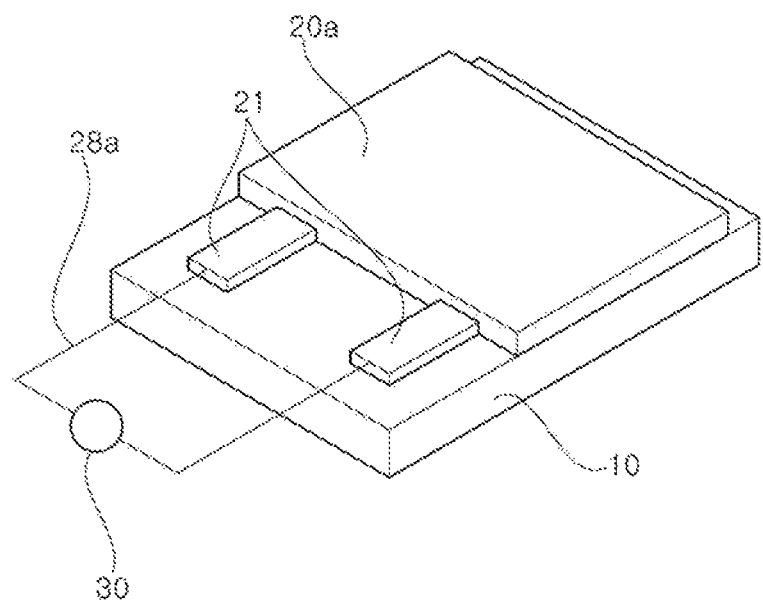
FIG. 2 is a perspective view showing a first example of a reactive coating layer of the apparatus for measuring the pollution level of the surface of the photovoltaic module according to the preferred embodiment of the present invention.
Figure 3:
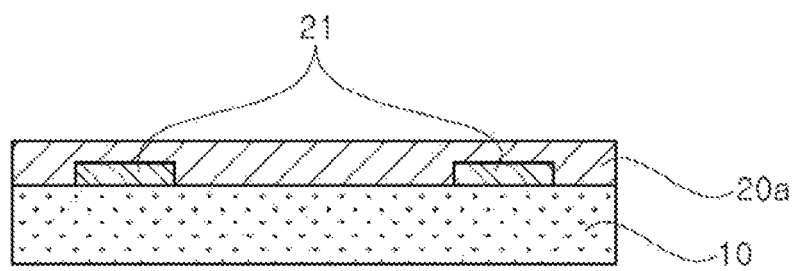
FIG. 3 is a sectional view showing the first example of the reactive coating layer of the apparatus for measuring the pollution level of the surface of the photovoltaic module according to the preferred embodiment of the present invention.

As shown in FIGS. 2 and 3, as a first example of the reactive coating layer 20, the reactive coating layer 20 includes a metal oxide layer 20a coated on the glass substrate 10 using oxide.

The metal oxide layer 20a is formed to cause the resistance change by physical and chemical reactions from the contact with the pollutants accumulated on one side thereof. That is, the metal oxide layer 20a is formed to derive an amount of the resistance change by the physical reaction and the chemical reaction happening between the metal oxide layer 20a and the accumulated pollutants.

There are copper oxide (CuO), titanium oxide ($TiO_2$), zinc oxide (ZnO) and so on as oxide applicable to the metal oxide layer 20a.

The metal oxide layer 20a may be formed to a thickness of 1 to 10 μm as occasion demands.

Electrode layers 21 are formed between the upper side of the glass substrate 10 and the metal oxide layer 20a of the reactive coating layer 20. That is, two electrode layers 21 are formed between the upper side of the glass substrate 10 and the metal oxide layer 20a to be spaced apart from each other in a lateral direction.

The electrode layers 21 are made from silver (Ag) which is a metal material.

First connection lines 28a are formed at ends of the electrode layers 21. That is, the first connection lines 28a are formed to electrically connect the electrode layers 21 to the signal processor 30 and transfer a sensing signal by the resistance change of the metal oxide layer 20a.

Figure 4:
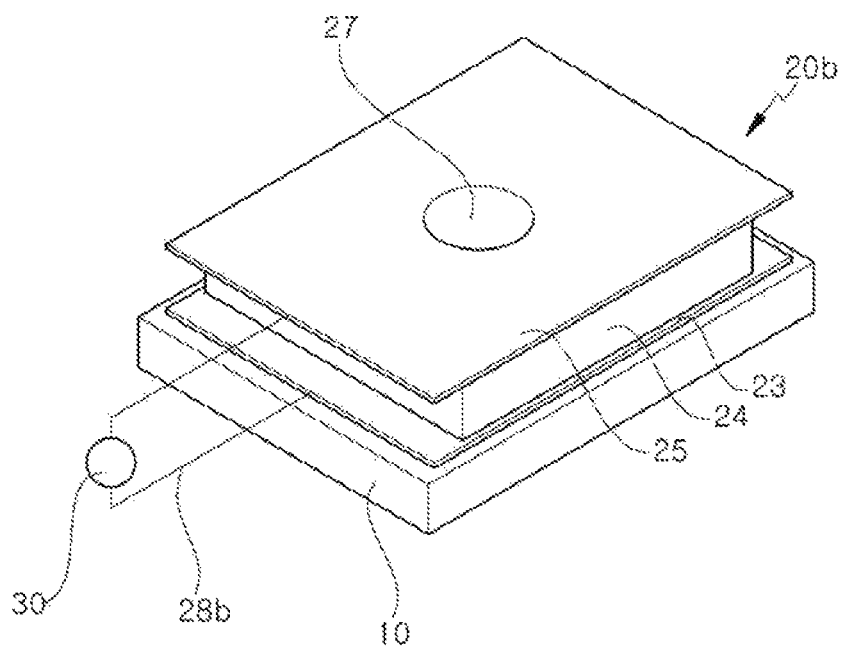
FIG. 4 is a perspective view showing a second example of the reactive coating layer of the apparatus for measuring the pollution level of the surface of the photovoltaic module according to the preferred embodiment of the present invention.
Figure 5:
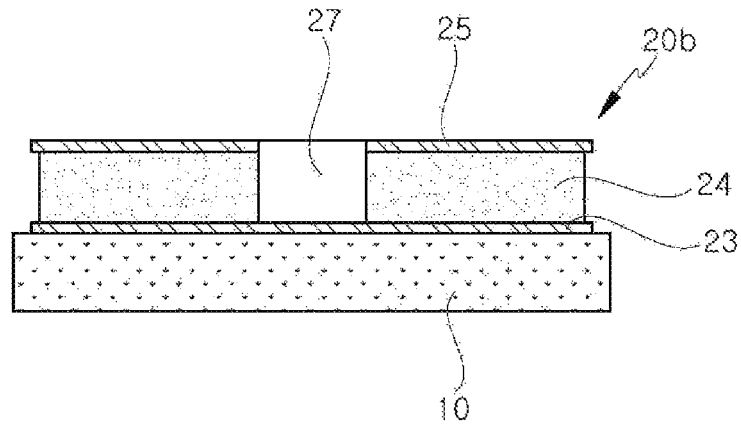
FIG. 5 is a sectional view showing the second example of the reactive coating layer of the apparatus for measuring the pollution level of the surface of the photovoltaic module according to the preferred embodiment of the present invention.

As shown in FIGS. 4 and 5, in a second example of the reactive coating layer 20, the reactive coating layer 20 includes a metal conductive layer 20b formed on the glass substrate 10 using electroconductive metal.

The metal conductive layer 20b is formed to cause a resistance change from the pollutants accumulated on one side thereof. That is, the metal conductive layer 20b causes the resistance change by a contact reaction of the pollutants which are nonconductive particles.

As shown in FIGS. 4 and 5, the metal conductive layer 20b includes: a first metal thin film layer 23 coated on the upper side of the glass substrate 10; a graphite conductive layer 24 disposed on the first metal thin film layer 23; and a second metal thin film layer 25 disposed on the graphite conductive layer 24.

The first metal thin film layer 23 and the second metal thin film layer 25 are still better in thermal conductivity than synthetic resin or ceramic and are made of a metallic material, such as aluminum or titanium.

It is preferable to use aluminum metal as a material to form the first metal thin film layer 23 and the second metal thin film layer 25.

The first metal thin film layer 23 and the second metal thin film layer 25 are respectively formed in a thin film type and have a thickness of about 0.5 to 2 μm.

The graphite conductive layer 24 is in the form of a plate having a predetermined thickness and is made of graphite which is a good conductor of electricity.

The metal conductive layer 20b has a hole 27 which is formed to induce pollutants to be accumulated. That is, the hole 27 is formed to measure the resistance change or a change of electricity accumulation between the electrode surfaces relative to the first metal thin film layer 23 and the second metal thin film layer 25.

The hole 27 has a structure that pollutants are accumulated therein and is formed to penetrate the metal conductive layer from the second metal thin film layer 25 to the graphite conductive layer 24. That is, a surface area of the second metal thin film layer 25 in which the hole 27 is formed and a surface area of the pollutants accumulated inside the hole 27 become a surface area of resistance relative to the upper side of the metal conductive layer 20b and a surface area of the first metal thin film layer 23 becomes a surface area of resistance relative to the lower side of the metal conductive layer 20b so as to generate a resistance value of a parallel connected type.

The hole 27 may be formed by one of various methods, such as etching or drilling.

Second connection lines 28b are formed at ends of the first metal thin film layer 23 and the second metal thin film layer 25. In other words, the second connection lines 28b are respectively derived from the first metal thin film layer 23 and the second metal thin film layer 25 and are electrically connected to the signal processor 30 so as to transfer the resistance change of the metal conductive layer 20b, namely, the sensing signal by the resistance value of the parallel connected type, to the signal processor 30.

The signal processor 30 operationally processes the signal of the reactive coating layer 20 and outputs a discrimination signal for pollution of the photovoltaic module.

The signal processor 30 is connected to the reactive coating layer 20 through the first connection lines 28a or the second connection lines 28b to transfer the signal of the resistance change.

Figure 6:
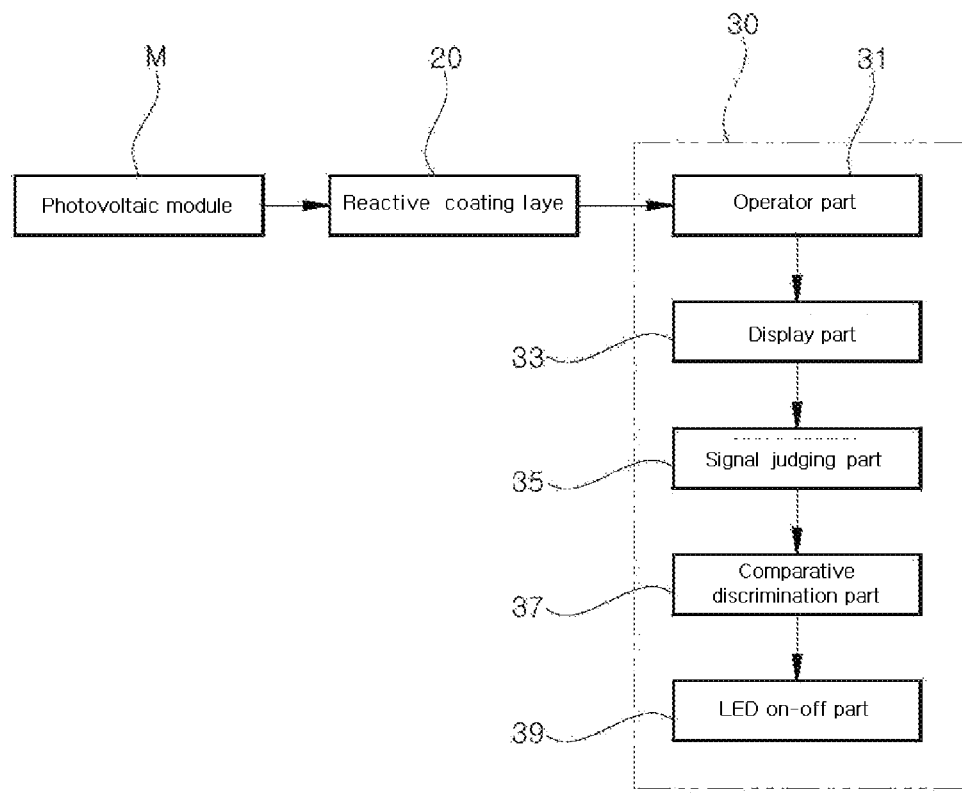
FIG. 6 is a block diagram showing the photovoltaic module according to the preferred embodiment of the present invention.

As shown in FIG. 6, the signal processor 30 is formed to measure a change amount of the resistance value from the resistance change due to accumulation of the pollutants on the photovoltaic module (M), and includes an operator part 31, a display part 33, a signal judging part 35, a comparative discrimination part 37 and an LED on-off part 39.

The operator part 31 operationally processes the resistance value from the signal inputted from the reactive coating layer 20 and measures and quantifies the pollution level. That is, the operator part 31 produces a resistance value from the resistance change varied according to accumulation of the pollutants on the reactive coating layer 20.

The display part 33 outputs the quantified resistance value measured in the operator part 31.

The display part 33 outputs a measured result of the operator part 31 in real time or outputs the measured result of the operator part 31 on a regular cycle.

The signal judging part 35 is formed to judge the change of the resistance value measured in the operator part 31. That is, the signal judging part 35 judges whether or not there is any change in the resistance values based on a resistance value before accumulation of the pollutants relative to the resistance value of the result measured in the operator part 31.

The comparative discrimination part 37 compares the resistance value measured in the operator part 31 with a reference resistance value set previously to discriminate pollution.

The comparative discrimination part 37 receives the resistance value measured in the operator part 31, and in this instance, the resistance value for discrimination is inputted to the comparative discrimination part 37 only when there is a change in the resistance value as a result of judgment through the signal judging part 35.

The comparative discrimination part 37 compares whether or not the resistance value causing the change in the signal judging part 35 is larger than the reference resistance value so as to judge whether or not to clean the photovoltaic module (M). For instance, if the resistance value inputted from the signal judging part 35 is larger than the reference resistance value, a signal to let a manager know it is necessary to clean the photovoltaic module is transferred to the LED on-off part 39.

The LED on-off part 39 turns light on and off to display the result in a recognizable form according to the discrimination signal of the comparative discrimination part 37.

The LED on-off part 39 uses LED lamps of various colors as a light on-off signal in order to display the final measurement result of the pollution level.

Figure 7:
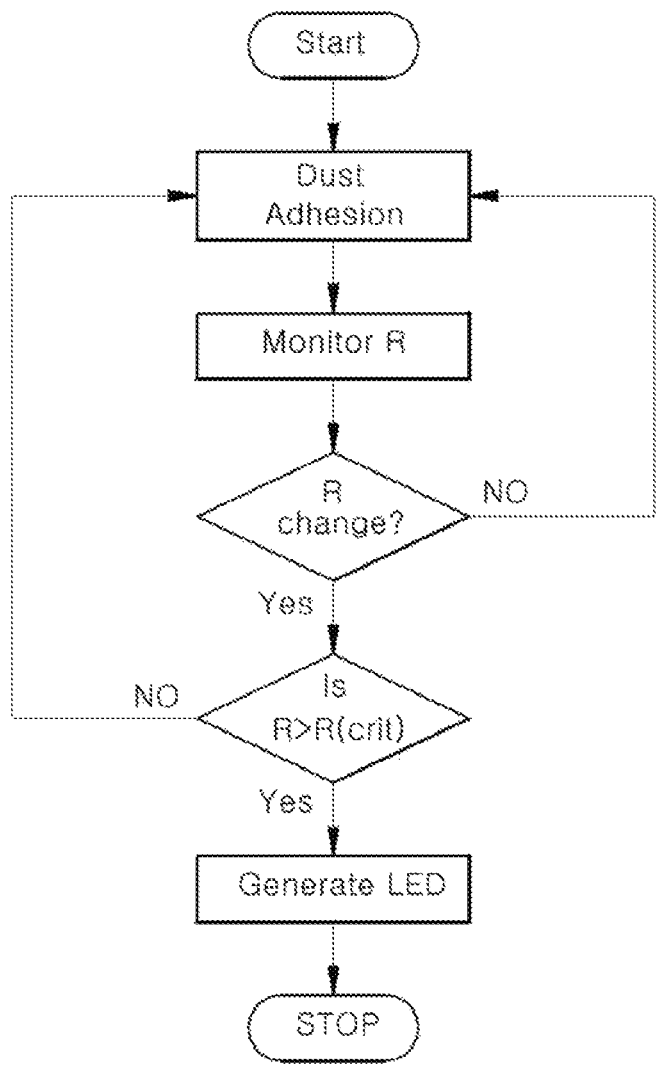
FIG. 7 is a flow chart showing an operation process of a signal processor of the apparatus for measuring the pollution level of the surface of the photovoltaic module according to the preferred embodiment of the present invention.

In other words, referring to FIG. 7, a processing process of the signal processor 30 will be described. First, in the state where the glass substrate 10 is located to get in contact with the surface of the photovoltaic module (M), measurement of the pollution level starts. A sensing signal of the resistance change is inputted to the operator part 31 of the signal processor 30 from the reactive coating layer 20, and then, the operator part 31 produces a resistance value by operationally processing the signal of the resistance change. Next, the resistance value operationally processed in the operator part 31 is outputted from the display part 33, and at the same time, the signal judging part 35 judges whether or not there is any change in the resistance value. In this instance, if the signal judging part 35 judges that there is no change in resistance value, measurement work is continued. However, if the signal judging part 35 judges that there is a change in resistance value, the comparative discrimination part 37 compares the measured resistance value with the reference resistance value to discriminate pollution. If the measured resistance value is larger than the reference resistance value, the final judgment result that it is necessary to clean the photovoltaic module is displayed through the LED on-off part 39.

In other words, because the apparatus for measuring the pollution level of the surface of the photovoltaic module according to the present invention discriminates pollution through the change amount of the resistance value after sensing the electric resistance change by contact with the pollutants, the pollution level measuring apparatus lets the manager know the optimum cleaning cycle to recognize necessity of cleaning work and maintain the photovoltaic module clean through the periodic cleaning work, thereby maintaining performance of equipment, lengthening the lifespan of equipment and increasing added value through energy generation by enhancing generation efficiency of the photovoltaic module.

Moreover, the apparatus for measuring the pollution level of the surface of the photovoltaic module according to the present invention can enhance price competitiveness by lowering manufacturing costs and installation costs of equipment because having the simple structure including the glass substrate attachable to the surface of the photovoltaic module, the reactive coating layer and the signal processor, and also enhance effectiveness of products because being flexibly applicable to previously designed photovoltaic modules.

Figure 8:
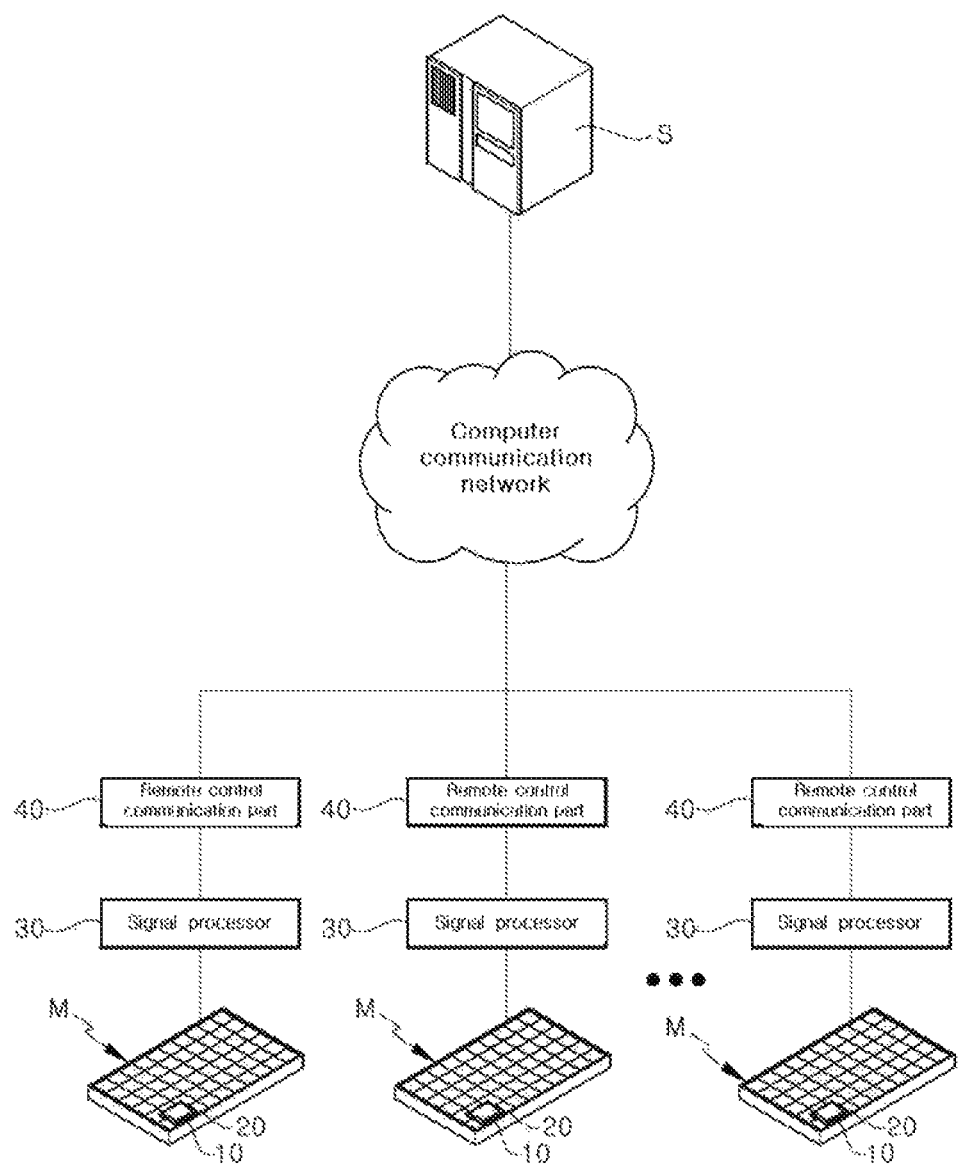
FIG. 8 is a schematic diagram of an apparatus for measuring the pollution level of the surface of a photovoltaic module according to another preferred embodiment of the present invention.

Furthermore, as shown in FIG. 8, the apparatus for measuring the pollution level of the surface of the photovoltaic module according to another preferred embodiment of the present invention further includes a remote control communication part 40 which is communicably connected with a central server (S) of a photovoltaic plant, in which a plurality of photovoltaic modules (M) are equipped in an array type.

The remote control communication part 40 is disposed to send and receive signals between the signal processor 30 and the central server (S). That is, the remote control communication part 40 is disposed on the signal processor 30 in order to send a signal to the central server (S) or to receive a signal from the central server (S).

The remote control communication part 40 sends and receives signals through a computer communication network with the central server (S). That is, the remote control communication part 40 sends the discrimination signal measured in the signal processor 30 to the central server (S) through the computer communication network, and receives a control signal of the central server (S) through the computer communication network so that the signal processor 30 can measure the pollution level.

For radio communication, the remote control communication part 40 adopts one of the associated press (AP) communication network or the long term evolution (LTE) communication network, which are general radio communications.

Due to the remote control communication part 40 which is communicably connected with the central server of the photovoltaic plant, the apparatus for measuring the pollution level of the surface of the photovoltaic module according to the present invention can measure the pollution level of the photovoltaic modules of the array type in a lump so as to easily maintain and rapidly process the measured result.

Other components of the pollution level measuring apparatus in accordance with the this embodiment are the same as those of the pollution level measuring apparatus in accordance with the above-described former embodiment, and a detailed description thereof will thus be omitted.

Although the preferred embodiments of the present invention have been disclosed for illustrative purposes, it will be understood by those of ordinary skill in the art that the protective scope of the present invention is not limited to the above embodiment and various changes and modifications may be made therein without departing from the technical idea and scope of the present invention and such changes and modifications belong to the claims of the present invention.

What is claimed is:

1. An apparatus to measure a pollution level of a surface of a photovoltaic module, comprising:
    a glass substrate attachably mounted on the surface of the photovoltaic module;
    a reactive coating layer coated on one side surface of the glass substrate comprises a structure to accumulate pollutants that cause a resistance change in the reactive coating layer;
    a signal processor connected to the reactive coating layer to receive a signal of the resistance change, configured to operationally process the signal of the reactive coating layer to measure a change in a resistance value of the reactive coating layer due to accumulated pollutants, and output a discrimination signal of the pollution level;
    wherein the reactive coating layer comprises a metal conductive layer formed from an electroconductive metal to cause the resistance change by a contact reaction with nonconductive particles of the accumulated pollutants; and
    wherein the metal conductive layer comprises a first metal thin film layer coated on an upper side of the glass substrate, a graphite conductive layer disposed on the first metal thin film layer, a second metal thin film layer disposed on the graphite conductive layer; and a hole formed to penetrate the metal conductive layer from the second metal thin film layer to the graphite conductive layer to induce the pollutants to be accumulated.

2. The apparatus to measure the pollution level according to claim 1, wherein the first metal thin film layer and the second metal thin film layer have a thickness of about 0.5 to 2 μm and are made of an aluminum metal.

3. The apparatus to measure the pollution level according to claim 1, further comprising connection lines which are respectively derived from the first metal thin film layer and the second metal thin film layer, and the connection lines are electrically connected to the signal processor.

4. The apparatus to measure the pollution level according to claim 1, wherein the signal processor further comprises:
    an operational part to operationally process the signal from the reactive coating layer to measure the resistance value;
    a display part to output the resistance value measured in the operational part;
    a signal judging part to determine whether there is any change in the resistance value measured in the operational part;
    a comparative discrimination part to compare the resistance value measured in the operational part with a reference resistance value set previously to discriminate the pollution level; and
    an LED on-off part to turn light on and off to display the result according to the discrimination signal outputted by the comparative discrimination part.

5. The apparatus to measure the pollution level according to claim 1, further comprising a remote control communication part communicably connected to a central server of a photovoltaic plant to transmit the discrimination signal measured in the signal processor to the central server through a computer communications network, and to receive a control signal from the central server through the computer communications network to instruct the signal processor to measure the pollution level.

* * * * *